(12) United States Patent
Kundra (10) Patent No.: US 8,013,114 B2
(45) Date of Patent: Sep. 6, 2011

(54) FUSION PROTEINS BASED UPON SOMATOSTATIN RECEPTORS

(75) Inventor: Vikas Kundra, Missouri City, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 878 days.

(21) Appl. No.: 11/610,378

(22) Filed: Dec. 13, 2006

(65) Prior Publication Data

US 2007/0161045 A1 Jul. 12, 2007

Related U.S. Application Data

(62) Division of application No. 10/076,267, filed on Feb. 14, 2002, now Pat. No. 7,176,187.

(60) Provisional application No. 60/268,600, filed on Feb. 15, 2001.

(51) Int. Cl.
 *C07K 14/71* (2006.01)
(52) U.S. Cl. ......... 530/311; 435/193; 435/194; 435/207
(58) Field of Classification Search ........................ None
 See application file for complete search history.

(56) References Cited

U.S. PATENT DOCUMENTS

| | | | |
|---|---|---|---|
| 5,331,094 A | 7/1994 | Eppler et al. | 530/395 |
| 5,693,679 A | 12/1997 | Vincent et al. | 530/311 |
| 5,846,819 A | 12/1998 | Pausch et al. | 435/320.1 |
| 5,998,154 A | 12/1999 | Schonbrunn | 435/7.21 |
| 6,008,012 A | 12/1999 | Bergsma et al. | 435/69.1 |
| 6,355,473 B1 * | 3/2002 | Ostanin et al. | 506/10 |
| 2001/0029035 A1 | 10/2001 | Eisenhut et al. | 435/69.4 |
| 2002/0151494 A1 * | 10/2002 | Shimkets et al. | 514/12 |
| 2003/0166061 A1 | 9/2003 | Glucksmann et al. | 435/69.1 |

OTHER PUBLICATIONS

Koenig et al., Biochem. J. (1998) vol. 336, pp. 291-298.*
Ausubel et al., In: *Short Protocols in Mol. Biol. 4th Ed.*, John Wiley & Sons, Inc., p. 9-27 and 9-31, 1999.
Coward et al., "Controlling signalling with specifically designed Gi coupled receptor," *Proc. Nat. Acad. Sci. USA*, 95:352-357, 1998.
Koller et al., "A generic method for the production of cell lines expressing high levels of 7-transmembrane receptors," *Analytical Biochemistry*, 250:51-60, 1997.
Kundra et al., "Noninvasive monitoring of somatostatin receptor type 2 chimeric gene transfer," *Journal of Nuclear Medicine*, 43: 406-412, 2002.
Praetor et al., "Intracellular traffice of the MHC class I-like IgG Fc receptor, FcRn, expressed in epithelial MDCK cells," *Journal of Cell Science*, 112: 2291-2299, 1999.
Rocheville et al., "Subtypes of the somatostatin receptor assemble as functional homo- and heterodimers," *Journal of Biological Chemistry*, 275: 7862-7869, 2000.
Rogers et al., "Evaluation of a n adenoviral vector encoding a model chimeric receptor as a receptor for imaging gene transfer," *Molecular Therapy*, 3(5), S57, Abstract No. 156, 2001.
Rogers et al., "Gene transfer strategies for improving radiolabeled peptide imaging and therapy," *The Quarterly Journal of Nuclear Medicine*, 44:208-223, 2000.
Rogers et al., "In vivo localization of [111in]-dtpa-d-phel-octreotide to human ovarian tumor xenografts induced to express the somatostatin receptor subtype 2 using an adenoviral vector," *Clinical Cancer Research*, 5:383-393, 1999.
Schindler et al., "Immunohistochemical localization of the somatostatin SST-2(A) receptor in the rat brain and spinal cord," *Neuroscience*, 76: 225-240, 1997.
Zinn et al., "Noninvasive monitoring of gene transfer using a reporter receptor imaged with high-affinity peptide radiolabeled with 99mTc or 188Re," *Journal of Nuclear Medicine*, 41: 887-895, 2000.
Kreienkamp et al., "Rat somatostatin receptor subtype 4 can be made sensitive to agonist-induced internalization by mutation of a single threonine (residue 331)," *DNA Cell Biology*, 17:869-78, 1998.
Nouel et al., "Differential internalization of somatostatin in COS-7 cells transfected with SSTI and SST2 receptor subtypes: a confocal microscopic study using novel fluorescent somatostatin derivatives," *Endocrinology*, 138:296-306, 1997.
Roth et al., "Endocytosis of the rat somatostatin receptors: subtype discrimination, ligand specificity, and delineation of carboxy-terminal positive and negative sequence motifs," *DNA Cell Biology*, 16:111-119, 1997.
Roth et al., "Phosphorylation of four amino acid residues in the carboxyl terminus of the rat somatostatin receptor subtype 3 is crucial for its desensitization and internalization," *J. Biol. Chem.*, 272: 23769-74, 1997.
Schwartkop et al., "Agonist-independent internalization and activity of a c-terminally truncated somatostatin receptor subtype 2 (Δ349)," *Journal of Neurochemistry*, 72:1275-82, 1999.

* cited by examiner

*Primary Examiner* — Jim Ketter
(74) *Attorney, Agent, or Firm* — Fulbright & Jaworski L.L.P.

(57) ABSTRACT

The present invention is directed to fusion proteins that can be used to assay gene transfer and expression both in vitro and in vivo. The fusion proteins contain a reporter protein, e.g. a somatostatin receptor, fused to a second protein, which may be a protein fusion tag. Alternatively, a fusion protein may be fused to a leader sequence. A leader sequence may localize an expressed protein, e.g localize a fusion protein to the cell membrane. The invention includes nucleic acids encoding the fusion proteins and methods of assaying for gene expression.

17 Claims, 1 Drawing Sheet

FIG. 1

FUSION PROTEINS BASED UPON SOMATOSTATIN RECEPTORS

CROSS-REFERENCE TO RELATED APPLICATION

This application is a divisional application of U.S. patent application Ser. No. 10/076,267, filed Feb. 14, 2002 now U.S. Pat. No. 7,176,187, which claims the benefit of priority to U.S. Provisional Patent Application Ser. No. 60/268,600 entitled "Fusion Proteins Based Upon the Somatostatin Type 2 Receptor" filed on Feb. 15, 2001, each of which is hereby incorporated by reference in its entirety.

FIELD OF THE INVENTION

The present invention is directed to fusion proteins containing a reporter polypeptide and to methods for using these fusion proteins to detect gene expression both in vitro and in vivo. The invention also includes fusion proteins in which the reporter is a somatostatin receptor (SSTR) or a SSTR that has been mutated by deleting all or part of its intracellular domain. In addition, a method is provided for creating and assaying receptor mutants.

BACKGROUND OF THE INVENTION

Before gene therapy can become clinically practical, methods will need to be developed for accurately assaying the in vivo expression of genes that have been delivered to a patient. Ideally, such methods should reveal not only where within the patient's body expression is occurring, but also whether it is taking place at a level and for a duration sufficient to be therapeutically effective. Most of the methods that have been developed thus far rely upon gamma-camera, SPECT or PET imaging to detect injected radiolabeled compounds. For example, Herpes simplex virus 1 thymidine kinase gene transfer has been followed using γ-camera imaging and positron emission tomography (PET) of radiolabeled prodrugs (Tjuvajek, et al., Cancer Res. 58:4333-4341 (1998); Alauddin, et al., Nucl Med. Biol. 25:175-180 (1998); Gambhir, et al., Med. Sci. 96:2333-2338 (1999)). Transfer of the type 2 dopamine receptor has been detected by PET using labeled antagonists (Gambhir, et al., Nucl. Med. Biol. 26:481-490 (1999); MacLaren, et al., Gene Ther. 6:785-791 (1999)) and transfer of a rat sodium/iodide symporter has been followed using a γ-camera to detect intracellularly trapped radioactive iodine (Mandell, et al., Cancer Res. 59:661-668 (1999)). One problem with many of these methods is that they either employ radiopharmaceuticals that are not known to be safe for use in humans or they use radioisotopes in ways that may have unforeseen adverse consequences.

Somatostatin receptors belong to a class of G-protein associated receptors having similar predicted three-dimensional structures consisting of seven transmembrane domains bridged by extracellular and intracellular loops. The somatostatin receptor family includes at least six distinct receptor subtypes encoded by five different genes, one of which generates two splice variant mRNAs. Gene sequences encoding human, rat, and, in some cases mouse somatostatin receptor (SSTR) subtypes 1, 2, 2b, 3, 4 and 5 have been published in the literature (Bruns et al., Ann. NY Acad. Sci., 733:138-146, 1994 and references cited therein). Accession numbers for exemplary mRNAs encoding these receptors can be found below.

The somatostatin type 2 receptor is characterized by the presence of an extracellular domain, seven transmembrane domains, and an intracellular domain that appears to be responsible for receptor internalization. The type 2 receptor is divided into two different subforms, 2 and 2b, that are identical except that type 2 has a longer C-terminal cytoplasmic (i.e. intracellular) domain. In vivo, the type 2 receptor has been detected using $^{111}$In-labeled octreotide (John, et al., Gut 38:33-39 (1995)), and somatostatin analogues labeled with either $^{99m}$Tc or [188]Re (Zinn, et al., JP Nucl Med. 41:887-895 (2000)). Currently, the [188]Re analog is not approved for therapeutic use by the FDA and the $^{99m}$Tc analog is only approved for imaging lungs. In contrast, $^{111}$In octreotide has been approved for total body imaging. Systems for following gene transfer which rely upon the imaging of a somatostatin receptor would provide a new tool for evaluating and monitoring gene therapy.

SUMMARY OF THE INVENTION

Figure 1:
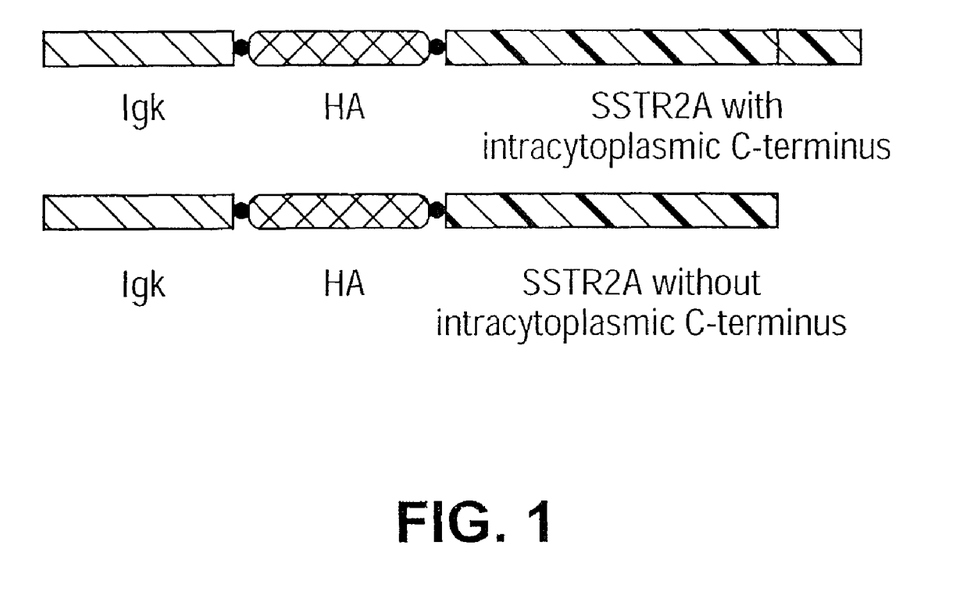
FIG. 1 shows the basic structural features that make up an exemplary fusion protein of the present invention. In the particular embodiment shown, and IgK domain is followed by a hemagglutinin A second polypeptide and then by the somatostatin type 2 receptor either with, or without, its cytoplasmic tail.

Embodiments of the invention include fusion proteins that can be used for quantitating gene transfer both in vitro and in vivo. Structural characteristics of exemplary proteins are shown in FIG. 1. At the C-terminal or N-terminal end of a fusion protein there may be a reporter polypeptide. As used herein, a reporter polypeptide ('reporter') is used to provide a signal that is used to detect gene transfer in vitro and/or in vivo. A reporter may be detected by a variety of methods, including but not limited to optical methods and in particular common radiological methods such as magnetic resonance imaging (MRI), computer tomography (CT), ultrasound, plain film and especially other techniques known to practitioners of nuclear medicine, such as gamma camera imaging, single photon emission tomography (SPECT) and positron emission tomography (PET). Signal generation may be the result of biophysical properties of a reporter and/or binding a labeled ligand, conversion of a prolabel, and/or sequestering or localizing a label in a cell expressing a nucleic acid construct encoding a fusion protein of interest. In certain embodiments a fusion protein may comprise an amino acid sequence coding for a ligand binding polypeptide. In particular embodiments, the reporter polypeptide is a SSTR polypeptide, such as subtypes 1, 2, 2b, 3, 4, and 5. In other embodiments the reporter polypeptide is a SSTR type 2 receptor. Reference to SSTR will include all subtypes unless otherwise indicated. The invention will work with a SSTR from any species and may employ all such receptors that have been described in the art at the present time. In certain embodiments, the human form of the receptor as disclosed by Yamada, et al. (Proc. Nat'l Acad. Sci. USA 89:251-255 (1992)) and Patel, et al. (Biochem. Biophys. Res. Commun. 192:288-294 (1993)) is used. In various embodiments, changes in the native somatostatin receptor may include changes that substantially alter its basic biological characteristics, for example ligand binding, antibody recognition and the like. In other embodiments variants of a SSTR may be used, for example, SSTR fusion proteins with all or part of the cytoplasmic tail of the receptor deleted. In particular embodiments all or part of the amino acid sequence lying C-terminal to residue 314 may be deleted.

The fusion protein may also comprise a second polypeptide fused to the N-terminal or C-terminal end of a reporter polypeptide (e.g. SSTR). Any protein or peptide can be used in this position, including those being evaluated for therapeutic potential. In other embodiments protein fusion tags ('tags') may be used. Tags may be chosen that are easily detected by immunological, biological, chemical or physical means. The second polypeptide may include, but is not limited to hemagglutinin A (HA), beta-galactosidase, thymidine kinase (TK), transferrin, myc-tags, VP16, (His)$_6$-tags chloramphenicol acetyl transferase (CAT), and other protein fusion tags known in the art. The tags may be detected by immunohistochemistry, western blotting, immunoprecipitation, immunolocalization, FACS analysis and other known immunological methods.

Trafficking of proteins through various transport routes in a cell is in part regulated by peptide targeting signal sequences, referred to herein as leader sequences. Leader sequences direct proteins to particular cellular organelles. For example, proteins destined for secretion from a cell are directed to the endoplasmic reticulum (ER) by a leader sequence referred to as a signal sequence. A signal sequence enables a protein to translocate across the ER membrane, either completely (i.e., into the lumen of the ER) or partially (i.e., remaining bound to the ER membrane by a transmembrane domain). In various non-limiting embodiments, the fusion protein comprises a leader sequence fused to a terminal end of the fusion protein. In particular embodiments the fusion protein comprises a leader sequence fused to the N-terminus of a fusion protein. The function of the leader is typically to guide the fusion protein to a particular, subcellular location. In particular embodiments, it guides a fusion protein to the cell membrane. In particular embodiments a leader sequence includes, but is not limited to IgK leader sequences. In particular embodiments, localization of a fusion protein to the cell membrane allows the fusion protein to be detected using labeled ligands that bind to the fusion proteins. Thus, expression may be assayed without the need for destroying cells.

Certain embodiments include nucleic acids that encode the fusion proteins described above. These nucleic acids may be incorporated into expression vectors in which they are operably linked to a promoter. The term "operably linked" refers to genetic elements that are joined in a manner that enables them to carry out their normal function. For example, a gene is operably linked to a promoter when its transcription is under the control of the promoter and such transcription ultimately produces the polypeptide normally encoded by the gene. The invention also includes host cells that have been transformed with expression vectors encoding the fusion protein(s) described.

Alternative embodiments may encompass methods of assaying gene expression by transfecting a host cell with an expression vector such as that described above and then detecting expression based upon the chemical, physical or biological properties of the encoded fusion protein. This method will be particularly effective when used in vivo and can be used for: a) identifying sites within a patient's body where expression is occurring; b) quantitating expression; and c) determining the duration of expression. For example, $^{111}$In-labeled octreotide administered to a patient or animal will bind to the somatostatin type 2 receptor portion of a fusion protein and can be detected using a γ-camera. The cytoplasmic tail of the receptor may be manipulated to alter specific signal to noise. In cases where a tag has been used as a second polypeptide in the fusion protein, the tag can be used to confirm results obtained by the binding of the ligand to a receptor. Using a protein fusion tag as the second polypeptide can also be used to compare expression in vitro with expression in vivo by normalizing the expression levels among mutants and comparing ligand binding affinities or antibody affinities for the mutants analyzed. Thus, mutants can be created with improved properties for reporting on gene transfer in vitro and in vivo. For example, hemagglutinin A (HA) may be detected using an antibody that binds with specificity to an HA tag. In other embodiments the second polypeptide may also be detected by a unique enzymatic activity, e.g., chloramphenicol acetyl transferase activity. The tag allows expression to be assayed independent of altered reporter protein properties, such as ligand binding or antibody recognition. In certain embodiments of the system, fusion proteins described herein may be used for developing mutants of reporter proteins and receptors other than the somatostatin receptor.

DESCRIPTION OF THE INVENTION

Embodiments of the present invention are directed to fusion proteins that can be used for tracking gene transfer and expression both in vitro and in vivo. Procedures for constructing DNA molecules encoding appropriately arranged fusion protein elements are well known in the art and plasmids that can be used for this purpose may be made using standard techniques in molecular biology (see e.g., Sambrook, et al., *Molecular Cloning: A Laboratory Manual*, 2$^{nd}$ ed., Cold Spring Harbor Press (1989)). DNA encoding the somatostatin receptor can be made synthetically or, alternatively, it can be cloned using PCR techniques such as those described in the Examples section below. The invention is compatible with any second polypeptide sequence and any leader sequence capable of directing proteins to cell membranes. Similarly, any type of promoter active in mammalian cells can be used in conjunction with the invention, including those that are inducible, repressible or constitutive. Preferred mammalian promoters include: that of the mouse metallothionein I gene (Hamer, et al., *J. Mol. Appl. Gen.* 1:273-288 (1982)); the immediate early and TK promoters of Herpes virus (Yao, et al., *J. Virol.* 69:6249-6258 (1995)); the SV 40 early promoter (Benoist, et al., *Nature* 290:304-310 (1981)); and the human CMV promoter (Boshart, et al., *Cell* 41:521-530 (1985)). Full length or minimal promoters may be used and other regulatory elements may be included. In general, it will be advisable to place a stop codon immediately after the nucleotides encoding the final C-terminal amino acid of the fusion protein to avoid the inclusion of extraneous amino acids unless a gene will be fused to a reporter.

After DNA encoding a reporter protein fusion, e.g. a SSTR fusion protein, has been incorporated into an expression vector, this vector may be introduced into cells by any means known in the art, including: calcium phosphate precipitation, microinjection, electroporation, liposomal transfer, viral transfer, non-viral transfer or by injection of naked DNA. Expression may then be detected using labeled ligands for a SSTR. In particular embodiments expression may be detected using a labeled ligand, e.g. labeled octreotide, for a somatostatin type 2 receptor.

Typically, an expression vector will be administered to a patient or an experimental animal by injection. In certain embodiments, expression vectors may be used to create transgenic or chimeric animals. Sites of gene transfer and expression may then be identified based upon the binding of detectably labeled ligand to a SSTR. In certain embodiments receptors with deletions in the cytoplasmic domain may be used. Detectable labels include, but are not limited to magnetic resonance agents, optical imaging agents, isotopes, radioisotopes, fluorescent compounds, enzymes, other labeling agents known in the art, or combinations thereof. In various embodiments $^{111}$In-labeled octreotide may be administered to a subject, which may be followed by tracking the ligand using a γ-camera (see Examples section).

Alternative methods for quantitating expression may also be used. For example, standard receptor binding assays may be performed on cell preparations. The essential feature of this method is that cells transformed with DNA expressing a SSTR-fusion protein are incubated with a detectably labeled ligand that binds with specificity to the SSTR receptor portion. Among the most commonly used fluorescent labeling compounds are rhodamine, phycoerythrin, phycocyanin, allophycocyanin, o-phthaldehyde, fluorescamine. Useful chemiluminescent compounds include luminol, isoluminol, theromatic acridinium ester, imidazole, acridinium salt, and oxalate ester. Useful enzymatic labels include but are not limited to horse radish peroxidase (HRP), alkaline phosphatase, etc. In particular embodiments $^{111}$In-octreotide is used as the ligand.

Nonspecific binding may be determined by carrying out the binding reaction in the presence of a large excess of unlabeled ligand. For example, isotopically labeled octreotide may be incubated with receptor in the presence of a large excess of unlabeled octreotide. Nonspecific binding should be subtracted from total binding, i.e. binding in the absence of unlabeled ligand for each sample tested. Other steps such as washing, stirring, shaking, filtering and the like may be included in assays as necessary. Assays may be performed at several concentrations of ligand in a range sufficient to perform a Scatchard analysis. This type of analysis is well known in the art and can be used for determining the number of receptors present (see e.g., Ausubel, et al., *Current Protocols in Molecular Biology*, 11.2.1-11.2.19 (1993)).

Fusion protein expression may also be confirmed by alternative means of detection. For example, antibodies directed at either the reporter portion or the second polypeptide portion of a fusion protein may be used to localize expression by immunofluorescence. Alternatively or in combination with, for example, SSTR detection, a protein fusion tag may be detected by immunological methods, including but not limited to western blotting, immunoprecipitation, immunohistochemistry, etc. Immunological methods may be used to sort, isolate, and/or identify cells that have been transfected by a vector encoding a fusion protein as described herein. Alternatively, a standard tag such as beta-galactosidase could be included as a fusion component and used for quantitation. Various fusion protein tags are available from vendors such as Santa Cruz Biotechnology (Santa Cruz, Calif.). Thus, in vitro assays might be used initially to determine the sites, amount and duration of expression in the cell followed by in vivo imaging of sites, duration and amount of expression in an animal. Tissue preparations may subsequently be used to confirm and quantitate results after the animal is sacrificed. In humans, imaging may provide information on location, duration and amount of expression.

Nucleic Acid Vectors

In certain embodiments the invention concerns vectors, or recombinant expression vectors, comprising any of the nucleic acid molecules described herein. Vectors are used herein either to amplify DNA or RNA encoding fusion proteins and/or to express DNA which encodes SSTR-fusion proteins. Vectors include, but are not limited to, plasmids, phages, cosmids, episomes, viral particles or viruses, and integratable DNA fragments (i.e., fragments integratable into the host genome by homologous recombination). Viral particles include, but are not limited to, adenoviruses, baculoviruses, parvoviruses, herpesviruses, poxviruses, adeno-associated viruses, Semliki Forest viruses, vaccinia viruses, retroviruses, microparticles and naked DNA. In various embodiments, expression may be targeted to a particular cell type or cell population by a targeting ligand. Expression vectors include, but are not limited to, pcDNA3 (Invitrogen) and pSVL (Pharmacia Biotech). Other expression vectors include, but are not limited to, pSPORT™ vectors, pGEM™ vectors (Promega), pPROEXvectors™(LTI, Bethesda, Md.), Bluescript™ vectors (Stratagene), pQE™ vectors (Qiagen), pSE420™ (Invitrogen), and pYES2™(Invitrogen). Expression constructs may comprise a fusion protein encoding polynucleotides operatively linked to an endogenous or exogenous expression control DNA sequence and a transcription terminator. Because of limited space for nucleic acid insertion in many vectors it may be desirable to insert smaller reporters or reporter fusion constructs. For example, deletion of all or part of the somatosatin receptor carboxy terminus may be used. Expression control DNA sequences include promoters, enhancers, operators, and regulatory element binding sites generally, and are typically selected based on the expression systems in which the expression construct is to be utilized. Promoter and enhancer sequences are generally selected for the ability to increase gene expression, while operator sequences are generally selected for the ability to regulate gene expression. Expression constructs of the invention may also include sequences encoding one or more selectable markers that permit identification of host cells bearing the construct. Expression constructs may also include sequences that facilitate homologous recombination in a host cell. In various embodiments constructs may also include sequences necessary for replication in a host cell.

Various exemplary tissue-specific promoters are listed herein (Pearse and Takor, 1979; Nylen and Becker, 1995). Although not a complete list, these promoters are exemplary of the types of promoters and enhancers that may be used in certain embodiments of the invention. Additional promoters, useful in the present invention, will be readily known to those of skill in the art. Enhancers include, but are not limited to Immunoglobulin Heavy Chain, Immunoglobulin Light Chain, T-Cell Receptor, HLA DQ α and DQ β, β-Interferon, Interleukin-2, Interleukin-2 Receptor, MHC Class II 5, MHC Class II HLA-DRα, β-Actin, Muscle Creatine Kinase, Prealbumin (Transthyretin), Elastase I, Metallothionein, Collagenase, Albumin Gene, α-Fetoprotein, τ-Globin, β-Globin, e-fos, c-HA-ras, Insulin, Neural Cell Adhesion Molecule (NCAM), α1-Antitrypsin, H2B (TH2B) Histone, Mouse or Type I Collagen, Glucose-Regulated Proteins (GRP94 and GRP78), Rat Growth Hormone, Human Serum Amyloid A (SAA), Troponin I (TN I), Platelet-Derived Growth Factor, Duchenne Muscular Dystrophy.

Inducible promoters include but are not limited to MT II, MMTV (mouse mammary tumor virus), c-jun, Collagenase, Stromelysin, Murine MX Gene, GRP78 Gene, α-2-Macroglobulin, Vimentin, MHC Class I Gene H-2kB, HSP70, Proliferin, Tumor Necrosis Factor, Thyroid Stimulating Hormone α, and Insulin E Box. Cell or tissue specific expression can be achieved by using cell-specific enhancers and/or promoters. See generally Huber et al. *Adv. Drug Delivery Reviews* 17:279-292, 1995.

Expression constructs may be utilized for production of an encoded protein, but may also be utilized simply to amplify an SSTR-fusion protein encoding polynucleotide sequence. In some embodiments, the vector is an expression vector wherein the polynucleotide is operatively linked to a polynucleotide comprising an expression control sequence. In certain embodiments autonomously replicating recombinant expression constructs such as plasmid and viral DNA vectors incorporating polynucleotides. Expression vectors may be replicable DNA constructs in which a DNA sequence encoding SSTR-fusion protein is operably linked or connected to suitable control sequences capable of effecting the expression of an SSTR-fusion protein in a suitable host. DNA regions are operably linked or connected when they are functionally related to each other. For example, a promoter is operably linked or connected to a coding sequence if it controls the transcription of the sequence. Amplification vectors do not require expression control domains, but rather need only the ability to replicate in a host, usually conferred by an origin of replication, and a selection gene to facilitate recognition of transformants. The need for control sequences in the expression vector will vary depending upon the host selected and the transformation method chosen. Generally, control sequences include a transcriptional promoter, an optional operator sequence to control transcription, a sequence encoding suitable mRNA ribosomal binding and sequences that controls the termination of transcription and translation.

In various embodiments vectors may contain a promoter that is recognized by the host organism. The promoter sequences may be prokaryotic, eukaryotic, synthetic or viral. Examples of suitable prokaryotic sequences include the $P_R$ and $P_L$ promoters of bacteriophage lambda (The bacteriophage Lambda, Hershey, A. D., Ed., Cold Spring Harbor Press, Cold Spring Harbor, N.Y. (1973); Lambda II, Hendrix, R. W., Ed., Cold Spring Harbor Press, Cold Spring Harbor, N.Y. (1980); the trp, recA, heat shock, and lacZ promoters of E. coli and the SV40 early promoter (Benoist et al. Nature, 290:304-310, 1981) . Additional promoters include, but are not limited to, mouse mammary tumor virus, long terminal repeat of human immunodeficiency virus, maloney virus, cytomegalovirus immediate early promoter, Epstein Barr virus, Rous sarcoma virus, human actin, human myosin, human hemoglobin, human muscle creatine, and human metalothionein.

Additional regulatory sequences may also be included in vectors. Examples of suitable regulatory sequences are represented by the Shine-Dalgarno of the replicase gene of the phage MS-2 and of the gene cII of bacteriophage lambda. The Shine-Dalgarno sequence may be directly followed by DNA encoding SSTR-fusion protein and result in the expression of the mature SSTR-fusion protein.

Moreover, suitable expression vectors can include an appropriate marker that allows the screening of the transformed host cells. The transformation of the selected host is carried out using any one of the various techniques well known to the expert in the art and described in Sambrook et al., supra.

An origin of replication may also be provided either by construction of the vector to include an exogenous origin or may be provided by the host cell chromosomal replication mechanism. If the vector is integrated into the host cell chromosome, the latter may be sufficient. Alternatively, rather than using vectors which contain viral origins of replication, one skilled in the art can transform mammalian cells by the method of co-transformation with a selectable marker and SSTR-fusion protein encoding DNA. An example of a suitable marker is dihydrofolate reductase (DBFR) or thymidine kinase (see, U.S. Pat. No. 4,399,216).

Nucleotide sequences encoding reporter protein fusions, such as SSTR2-fusion proteins, may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulation are disclosed by Sambrook et al., supra and are well known in the art. Methods for construction of mammalian expression vectors are disclosed in, for example, Okayama et al., Mol. Cell. Biol., 3:280, 1983; Cosman et al., Mol. Immunol., 23:935, 1986; Cosman et al., Nature, 312:768, 1984; EP-A-0367566, and WO 91/18982.

Nucleic Acid Delivery

Liposomal Formulations

In certain embodiments, the oligo- or polynucleotides and/or expression vectors may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, In: Liver Diseases, Targeted Diagnosis and Therapy Using Specific Receptors and Ligands, Wu et al. (Eds.), Marcel Dekker, New York, pp 87-104, 1991). Also contemplated are cationic lipid-nucleic acid complexes, such as lipofectamine-nucleic acid complexes.

In certain embodiments of the invention, the liposome may be complexed with a hemagglutinating virus (HVJ). This has been shown to facilitate fusion with the cell membrane and promote cell entry of liposome-encapsulated DNA (Kaneda et al., Science, 243:375-378, 1989). In other embodiments, the liposome may be complexed or employed in conjunction with nuclear non-histone chromosomal proteins (HMG-1) (Kato et al., J. Biol. Chem., 266:3361-3364, 1991). In yet further embodiments, the liposome may be complexed or employed in conjunction with both HVJ and HMG-1. In that such expression vectors have been successfully employed in transfer and expression of a polynucleotide in vitro and in vivo, then they are applicable for the present invention. Where a bacterial promoter is employed in the DNA construct, it also will be desirable to include within the liposome an appropriate bacterial polymerase.

"Liposome" is a generic term encompassing a variety of single and multilamellar lipid vehicles formed by the generation of enclosed lipid bilayers. Phospholipids are used for preparing the liposomes according to the present invention and can carry a net positive charge, a net negative charge or are neutral. Dicetyl phosphate can be employed to confer a negative charge on the liposomes, and stearylamine can be used to confer a positive charge on the liposomes.

Lipids suitable for use according to the present invention can be obtained from commercial sources. For example, dimyristyl phosphatidylcholine ("DMPC") can be obtained from Sigma Chemical Co., dicetyl phosphate ("DCP") is obtained from K & K Laboratories (Plainview, N.Y.); cholesterol ("Chol") is obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform, chloroform/methanol or t-butanol can be stored at about −20° C. In certain embodiments, chloroform is used as the only solvent since it is more readily evaporated than methanol.

Liposomes used according to the present invention can be made by different methods. The size of the liposomes varies depending on the method of synthesis. A liposome suspended in an aqueous solution is generally in the shape of a spherical vesicle, having one or more concentric layers of lipid bilayer molecules. Each layer consists of a parallel array of molecules represented by the formula XY, wherein X is a hydrophilic moiety and Y is a hydrophobic moiety. In aqueous suspension, the concentric layers are arranged such that the hydrophilic moieties tend to remain in contact with an aqueous phase and the hydrophobic regions tend to self-associate. For example, when aqueous phases are present both within and without the liposome, the lipid molecules will form a bilayer, known as a lamella, of the arrangement XY-YX.

Liposomes within the scope of the present invention can be prepared in accordance with known laboratory techniques. In one embodiment, liposomes are prepared by mixing liposomal lipids, in a solvent in a container, e.g., a glass, pear-shaped flask. The container should have a volume ten-times greater than the volume of the expected suspension of liposomes. Using a rotary evaporator, the solvent is removed at approximately 40° C. under negative pressure. The solvent normally is removed within about 5 min to 2 hours, depending on the desired volume of the liposomes. The composition can be dried further in a desiccator under vacuum. The dried lipids generally are discarded after about 1 week because of a tendency to deteriorate with time.

Dried lipids can be hydrated at approximately 25-50 mM phospholipid in sterile, pyrogen-free water by shaking until all the lipid film is resuspended. The aqueous liposomes can be then separated into aliquots, each placed in a vial, lyophilized and sealed under vacuum.

In the alternative, liposomes can be prepared in accordance with other known laboratory procedures: the method of Bangham et al., *J. Mol Biol* 13:238-252, 1965; the method of Gregoriadis, as described in *Drug Carriers In Biology And Medicine*, G. Gregoriadis ed. (1979) pp. 287-341; the method of Deamer and Uster In. *Liposomes*; M. Ostro, ed., 1983; and the reverse-phase evaporation method as described by Szoka et al., *Proc. Natl. Acad. Sci. USA*, 75:4194-4198, 1978. The aforementioned methods differ in their respective abilities to entrap aqueous material and their respective aqueous space-to-lipid ratios.

The dried lipids or lyophilized liposomes prepared as described above may be reconstituted in a solution of nucleic acid and diluted to an appropriate concentration with an suitable solvent, e.g., DPBS. The mixture is then vigorously shaken in a vortex mixer. Unencapsulated nucleic acid is removed by centrifugation at 29,000× g and the liposomal pellets washed. The washed liposomes are resuspended at an appropriate total phospholipid concentration, e.g., about 50-200 mM. The amount of nucleic acid encapsulated can be determined in accordance with standard methods. After determination of the amount of nucleic acid encapsulated in the liposome preparation, the liposomes may be diluted to appropriate concentration and stored at 4° C. until use.

Alternative Delivery Systems

Viral Methods

Human adenoviruses are double-stranded DNA tumor viruses with genome sizes of approximate 36 kB (Tooze, *Molecular Biology of DNA Tumor Viruses*, 2$^{nd}$ ed., Cold Spring Harbor Laboratory, Cold Spring Harbor, N.Y., 1991). As a model system for eukaryotic gene expression, adenoviruses have been widely studied and well characterized, which makes them an attractive system for development of adenovirus as a gene transfer system. This group of viruses is easy to grow and manipulate, and they exhibit a broad host range in vitro and in vivo. In lytically infected cells, adenoviruses are capable of shutting off host protein synthesis, directing cellular machineries to synthesize large quantities of viral proteins, and producing copious amounts of virus.

The E1 region of the genome includes E1A and E1B which encode proteins responsible for transcription regulation of the viral genome, as well as a few cellular genes. E2 expression, including E2A and E2B, allows synthesis of viral replicative functions, e.g. DNA-binding protein, DNA polymerase, and a terminal protein that primes replication. E3 gene products prevent cytolysis by cytotoxic T cells and tumor necrosis factor and appear to be important for viral propagation. Functions associated with the E4 proteins include DNA replication, late gene expression, and host cell shutoff. The late gene products include most of the virion capsid proteins, and these are expressed only after most of the processing of a single primary transcript from the major late promoter has occurred. The major late promoter (MLP) exhibits high efficiency during the late phase of the infection (Stratford-Perricaudet and Perricaudet, In: *Human Gene Transfer*, eds., John Libbey Eurotext, France, pp. 51-61, 1991).

As only a small portion of the viral genome appears to be required in cis (Tooze, 1981), adenovirus-derived vectors offer excellent potential for the substitution of large DNA fragments when used in connection with cell lines such as 293 cells. Ad5-transformed human embryonic kidney cell lines (Graham, et al, *J. Gen. ViroL*, 36:59-72, 1977) have been developed to provide the essential viral proteins in trans.

Particular advantages of an adenovirus system for delivering foreign proteins to a cell include (i) the ability to substitute relatively large pieces of viral DNA by foreign DNA; (ii) the structural stability of recombinant adenoviruses; (iii) the safety of adenoviral administration to humans; and (iv) lack of any known association of adenoviral infection with cancer or malignancies; (v) the ability to obtain high titers of the recombinant virus; and (vi) the high infectivity of adenovirus.

Further advantages of adenovirus vectors over retroviruses include the higher levels of gene expression. Additionally, adenovirus replication is independent of host gene replication, unlike retroviral sequences. Because adenovirus transforming genes in the E1 region can be readily deleted and still provide efficient expression vectors, oncogenic risk from adenovirus vectors is thought to be negligible (Grunhaus & Horwitz, *Seminar in Virology*, 3:237-252, 1992).

In general, adenovirus gene transfer systems are based upon recombinant, engineered adenovirus which is rendered replication-incompetent by deletion of a portion of its genome, such as E1, and yet still retains its competency for infection. Sequences encoding relatively large foreign proteins can be expressed when additional deletions are made in the adenovirus genome. For example, adenoviruses deleted in both E1 and E3 regions are capable of carrying up to 10 kB of foreign DNA and can be grown to high titers in 293 cells (Stratford-Perricaudet and Perricaudet, 1991). Surprisingly persistent expression of transgenes following adenoviral infection has also been reported.

Other viral vectors may be employed as expression constructs in the present invention. Vectors derived from viruses such as vaccinia virus (Ridgeway, In. *Vectors: A survey of molecular cloning vectors and their uses*, Rodriguez R L, Denhardt D T, ed., Stoneham:Butterworth, pp. 467-492, 1988.; Baichwal and Sugden, In: *Gene Transfer*, Kucherlapati R, ed., New York, Plenum Press, pp. 117-148, 1986.; Coupar et al., *Gene*, 68:1-10, 1988) adeno-associated virus (AAV) (Ridgeway, 1988; Baichwal and Sugden, 1986; Hermonat and Muzycska, *Proc. Nat. Acad. Sci. USA*, 81:6466-6470, 1984) and herpes viruses may be employed. They offer several attractive features for various mammalian cells (Friedmann, *Science*, 244:1275-1281, 1989; Ridgeway, 1988; Baichwal and Sugden, 1986; Coupar et al., 1988; Horwich et al., *J. Virol*, 64:642-650, 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al. recently introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al., *Hepatology,* 14:124A, 1991).

Non-viral Methods

Several non-viral methods for the transfer of expression vectors into cultured mammalian cells also are contemplated by the present invention. These include calcium phosphate precipitation (Graham and Van Der Eb, *Virology,* 52:456-467, 1973; Chen and Okayama, *Mol. Cell Biol.,* 7:2745-2752, 1987; Rippe et al., *Mol Cell Biol.,* 10:689-695, 1990) DEAE-dextran (Gopal, *Mol. Cell BioL,* 5:1188-1190, 1985), lipofectamine-DNA complexes, and receptor-mediated transfection (Wu and Wu, *J. Biol Chem.,* 262: 4429-4432, 1987; Wu and Wu, *Biochemistry,* 27: 887-892, 1988). Some of these techniques may be successfully adapted for in vivo or ex vivo use.

In one embodiment of the invention, the expression construct may simply consist of naked recombinant vector. Transfer of the construct may be performed by any of the methods mentioned above which physically or chemically permeabilize the cell membrane. For example, Dubensky et al. (1984) successfully injected polyomavirus DNA in the form of CaPO4 precipitates into liver and spleen of adult and newborn mice demonstrating active viral replication and acute infection (Dubensky et al., *Proc. Nat. Acad. Sci. USA,* 81:7529-7533, 1984). Benvenisty and Neshif (1986) also demonstrated that direct intraperitoneal injection of CaPO4 precipitated plasmids results in expression of the transfected genes (Benvenisty and Neshif, *Proc. Nat. Acad. Sci. USA,* 83:9551-9555, 1986). In alternative embodiments a cell may be used as a delivery vector. A cell may be transfected in vitro, harvested, and injected into an appropriate location in a host animal or human. Cells that may be used as delivery vehicles include but are not limited to stem cells, spleen cells, and other cells that may target, incorporate, or otherwise provide therapy to tissue or organ of an animal or human. Stem cells may also be used for creating transgenic or chimeric animals.

Targeting ligands may be selected from a wide variety of moieties capable of targeting the delivery vector to a selected cell or tissue. Examples of suitable ligands include, but are not limited to the following: Polyamino polymers (Goldman et al., *Nat. Biotechnol.* 15:462-466, 1997), (e.g. polylysine (Kollen et aL, *Hum. Gene. Ther.* 7:1577-1586, 1996)); folate; water soluble vitamins; Pyridoxyl phosphate; Apolipoproteins; Insulin; Transferrin; Galactose; Sialic acid; Mac-1; VEGF; basic FGF; EGF; VCAM-1; ICAM-1; PECAM-1/CD31; Fibronectin; Osteopontin; RGD peptides; peptide mimetics; HIV GP 120/41 or GP120; Anti-cell surface receptor antibodies (or fragments thereof), such as anit-HER2/neu, anti-selectin, Anti-cell surface receptor antibodies (fragments thereof) (e.g. antibodies to CD34, CD19, CD4, CD7, CDB, CD20, CD22).

In various embodiments a ligand may be an antibody or an antibody fragment. It will be appreciated that the antibody or antibody fragment may be of mouse origin and humanized to remove murine surface recognition features.

In another embodiment, the targeting ligand binds to an extracellular domain of a growth factor receptor. Exemplary receptors include the c-erbB-2 protein product of the HER2/neu oncogene, epidermal growth factor (EGF) receptor, basic fibroblast growth receptor (basic FGF) receptor and vascular endothelial growth factor receptor, E-, L- and P-selectin receptors, folate receptor, CD4 receptor, CD19 receptor, αβintegrin receptors and chemokine receptors.

A targeting ligand may be covalently attached to a viral or non-viral nucleic acid delivery vector. There are various techniques for attaching a selected targeting ligand. For example, the hydrophilic polymer polyethyleneglycol (PEG) has been widely studied (Allen, T. M., et al., Biochemicia et Biophysica Acta 1237:99-108 (1995); Zalipsky, S., Bioconjugate Chem., 4(4):296-299 (1993); Zalipsky, S., et al., FEBS Lett. 353:71-74 (1994); Zalipsky, S., et al., Bioconjugate Chemistry, 705-708 (1995); Zalipsky, S., in STEALTH LIPOSOMES (D. Lasic and F. Martin, Eds.) Chapter 9, CRC Press, Boca Raton, Fla. (1995)).

Generally, a delivery vector may be functionalized to contain reactive groups suitable for coupling with, for example, sulfhydryls, amino groups, and aldehydes or ketones present in a wide variety of ligands. Examples of PEG-terminal reactive groups include maleimide (for reaction with sulfhydryl groups), N-hydroxysuccinimide (NHS) or NHS-carbonate ester (for reaction with primary amines), hydrazide or hydrazine (for reaction with aldehydes or ketones), iodoacetyl (preferentially reactive with sulfhydryl groups) and dithiopyridine (thiol-reactive). Synthetic reaction schemes for activating PEG with such groups are set forth in U.S. Pat. Nos. 5,631,018, 5,527,528, 5,395,619. Other ligands such as peptides may be encoded in a gene that codes for a structural component of a virus or other delivery vector, such as coat proteins. Patents WO 98/39464, WO 98/39465, and WO 98/39467 discuss methods for targeting specific cell populations to express a protein of interest.

Pharmaceutical Compositions And Routes Of Administration

Where clinical application of an expression construct comprising a nucleic acid encoding SSTR-fusion protein is contemplated, it will be necessary to prepare the complex as a pharmaceutical composition appropriate for the intended application. Generally this will entail preparing a pharmaceutical composition that is essentially free of pyrogens, as well as any other impurities that could be harmful to humans or animals. One also will generally desire to employ appropriate salts and buffers to render the complex stable and allow for complex uptake by target cells.

Aqueous compositions of the present invention comprise an effective amount of the expression construct, dissolved or dispersed in a pharmaceutically acceptable carrier or aqueous medium. Such compositions can also be referred to as inocula. The phrases "pharmaceutically or pharmacologically acceptable" refer to molecular entities and compositions that do not produce an adverse, allergic or other untoward reaction when administered to an animal, or a human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the pharmaceutical compositions is contemplated. Supplementary active ingredients also can be incorporated into the compositions.

Solutions of the active compounds as free base or pharmacologically acceptable salts can be prepared in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations contain a preservative to prevent the growth of microorganisms.

The expression constructs and delivery vehicles of the present invention may include classic pharmaceutical preparations. Administration of compositions according to the present invention will be via any common route so long as the target tissue is available via that route. This includes oral, nasal, buccal, rectal, vaginal or topical. Alternatively, administration may be by orthotopic, intradermal, subcutaneous, intramuscular, intraperitoneal, percutaneous or intravascular methods. Such compositions would normally be administered as pharmaceutically acceptable compositions that include physiologically acceptable carriers, buffers or other excipients.

The compositions of the present invention may be advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like. Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components of the pharmaceutical composition are adjusted according to known parameters.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders. When the route is topical, the form may be a cream, ointment, salve or spray.

An effective amount of the composition is determined based on the intended goal, for example (i) assay gene expression in vitro or (ii) assay gene expression in vivo. The term "unit dose" refers to physically discrete units suitable for use in a subject, each unit containing a predetermined-quantity of the composition calculated to produce the desired responses, discussed above, in association with its administration, i.e., the appropriate route and administration regimen. The quantity to be administered, both according to number of administrations and unit dose, depends on the subject and the state of the subject. Precise amounts of the composition also depend on the judgment of the practitioner and are peculiar to each individual.

EXAMPLES

Materials and Methods

Cloning phage containing the SSTR2A insert (American Type Culture Collection) using a forward primer (TCC CCG CGG CAT GGA CAT GGC GGA TGA, SEQ ID NO:1) that contains a Sac II restriction site and a reverse primer (AAT CTG CAG CTG TCA GAT ACT GGT TTG GAG, SEQ ID NO:2) that contains a Pst I restriction site and a stop codon. A second oligonucleotide, TM7IB which excludes almost all of the SSTR2A intracellular domain except for phenylalanine 314, was also used. This oligonucleotide also contains a Pst I restriction site and a stop codon. The full length or "intracellular tail minus" SSTR2A insert was ligated to the pDisplay vector (Invitrogen). The insert is placed downstream of a membrane localization sequence (IgK leader) and of a hemagglutinin A (HA) epitope tag. Next, Top 10 cells (Invitrogen) were transformed using either vector alone or vector containing the SSTR2 insert using calcium chloride and then selected for ampicillin resistance. Midipreps were performed using the Promega Midiprep kit.

Cell Lines

HT 1080 cells, a human fibroblast cell line, were grown in DMEM containing 1× glutamine, penicillin, streptomycin (GPS) and 10% fetal bovine serum. For transfections, 1 µg of DNA was added with lipofectin (Gibco BRL) according to the manufacturer's instructions. After 5 hours, the lipofectin-DNA solution was washed and the cells incubated in DMEM, 1× GPS and 10% FBS for an additional two days. The cells were then split 1:20 and 1:5 and single colonies were picked after G418 selection.

Enzynme Linked Immunosorbent Assay (ELISA)

Colonies were tested for expression by ELISA. Confluent 96 well plates were washed twice with PBS and fixed for 30 minutes with 2% formaldehyde in PBS or 10% formalin. They were washed twice with PBS and then blocked with 5% milk for 30 minutes. After one wash in PBS, the cells were exposed to 50 mU/ml HRP-rat-anti-HA antibody (clone 3F10 from Roche) overnight at 4° C. or for one hour at room temperature. Three washes with PBS for 5 minutes each followed. Positive cells exhibited a green color product after exposure to the HRP ELISA substrate. The method was modified to quantitatively assay for the presence of the HA domain. 30,000 cells per well of a 96 well plate were processed as above. After developing the color reaction, optical density at 405 nm was compared to a standard curve constructed using HRP-rat-anti-HA antibody dilutions. The linear portion of the curve gave an $R^2$ value greater than 0.95.

Dot Blots and Western Blots

Confluent six well dishes were washed with PBS and then exposed to Triton X-100/SDS lysis solution (0.1% sodium dodecyl sulfate, 1% Triton, 0.1M Tris (pH8), 0.14M sodium chloride, 0.025% sodium azide, 0.18% complete protease inhibitor, 1M iodoacetamide) for one hour at 4° C. After a 30 minute, 14,000 g centrifugation, the supernatant was collected and the protein concentration determined using the Bradford method. Twenty micrograms of protein were loaded per lane on 7% SDS gels. Afterwards, protein was transferred to nitrocellulose using a semi-dry transfer apparatus and Towbin buffer. The blots were dried and transfer was confirmed with Ponceau-S staining. For dot blots, 15 µg of protein from the cell lysate were pipetted onto nitrocellulose and air dried. Next, the membrane for the dot blot or Western blot was washed with PBS and blocked with 5% milk for one hour at room temperature. After one wash in PBS with 0.1% Tween, the cells were exposed to 50 mU/ml HRP-rat-anti-HA antibody (clone 3 F10 Roche) overnight at 4° C. or for one hour at room temperature. After incubation, four washes were performed with PBS for 5 minutes each and the membrane was covered with a chemiluminescent HRP substrate for filming.

Immunofluorescence

Overnight, 10,000 cells were plated per well in an eight well silicone chamber slide system. Cells were fixed with 10% formalin for 30 minutes, washed with PBS twice and blotted with 5% milk for 30 minutes. Cells were then exposed to 1:250 diluted mouse anti-HA antibody for one hour at room temperature. Five washes were then performed for 5 minutes each. Next, 1:150 diluted FITC-goat anti-mouse antibody was placed on the cells. Again, five washes were then performed for 5 minutes each. The slide was then mounted with a coverslip in preparation for the evaluation of immunofluorescence.

Receptor Binding Studies

Overnight, 30,000 cells were plated per well of a 96 well plate. Following a PBS wash, they were exposed to $1 \times 10^{-7}$M $^{111}$In-octreotide or $^{111}$In-octreotide with $1 \times 10^{-6}$M somatostatin-28 in binding buffer (20 mM Hepes (pH 7.4), 0.1% bacitracin, 0.2% BSA) at room temperature. After one hour, the cells were washed with PBS five times and then lysed with 0.1N NaOH. A gamma-counter was used to determine radioactive decay. Controls included cells exposed to binding buffer without radioactivity and wells without cells that were exposed to binding buffer with radioactivity. Plates were observed after each wash to monitor cell loss.

Biodistribution and Imaging

In nude mice, subcutaneous injection of $5 \times 10^{-6}$ cells produced palpable tumors after one week. 350 µCi or 10 µCi $^{111}$In-octreotide were injected per mouse via the tail vein. 24 hours later, mice were sacrificed and dissected. Each organ and tumor was weighed and radioactive decay was determined using a gamma counter. One tailed t-tests were used to compare significant differences in biodistribution among tumors given known differences in expression. Four hours and 24 hours after $^{11}$. In-octreotide injection, sedated mice were imaged for 10 minutes with a γ-camera (GE Starcam 3200) fitted with a medium energy pinhole collimator.

Results

Cloning

The full length or intracellular tail minus SSTR2A receptor was cloned into the pDisplay vector containing a 5' IgK leader sequence for membrane localization of the expressed protein. The leader sequence is followed by a hemagglutinin A sequence for antibody-based detection. The binding domain for octreotide is predicted to primarily involve the carboxy portion of the receptor between transmembrane domains 3-7. Thus, amino terminal fusion of the receptor is less likely to interfere with binding; in addition, it is less likely to interfere with receptor internalization, which is dependent upon the carboxy terminal intracellular domain (Koenig, et al., Biochem. J. 336:291-298; Roth, et al., DNA and Cell Biology 16:111-119 (1997)). In order to prevent expression beyond the C-terminus of SSTR2A, a stop codon was introduced into the PCR back primer. After cloning SSTR2 into pDisplay, the vector or the vector plus insert was introduced into HT1080 cells using lipofectin and G418 selection. The fusion protein product consists of a 5' IgK leader sequence, an HA domain, and SSTR2A with or without the intracytoplasmic C-terminal tail.

Expression

Expression was confirmed in whole cells by ELISA and in cell lysates by dot blots and Western blots. The data obtained indicated that, of cell clones expressing full length SSTR2A fusion protein, "clone 21" had the highest level of expression followed by "clone 3" and then by "clone 11." For example, in a quantitative ELISA using an antibody to the HA domain, clone 21 reacted more than clone 3 which reacted more than clone 11. No reaction was seen in cells transfected with vector alone. The measurements were compared to an HRP-conjugated antibody dilution curve with an $R^2$ value of 0.98.

By dot blot, clone 21 was found to have a greater signal than clone 3, which had greater signal than clone 11. Clones in which the cytoplasmic tail of the receptor had undergone deletion (clone "tail-4" and clone "tail-1") were also found to give significant signals in dot blots. Clone tail-4 had greater signal than clone tail-1. In comparison to full length SSTR2A fusion proteins, clone tail-4 has less signal than clone 21 and clone tail-1 has less signal than clone 11. No signal was seen in cells transfected with vector only. This pattern of expression was also found in the ELISA and in Western blots. Further, in Western blots, a distinct band was observed in all lanes representing cells transfected with the full length or tail minus SSTR2 chimeric gene, but not in lanes containing material from cells transfected with vector alone. The greater than predicted molecular weight of the expressed fusion proteins (72 kD for full length SSTR2A fusion protein and 70 kD for tail-SSTR2 fusion protein) is likely due to aberrant glycosylation secondary to the amino terminus fusion. However, as demonstrated above, this does not prevent ligand binding.

Immunofluorescence

In order to determine the cellular localization of the expressed protein, the HA tag was targeted by immunofluorescence. The tag was detected in cells transfected with the full length SSTR2A or tail minus gene chimera but not in cells transfected with vector alone or in cells that did not undergo transfection at all. Immunofluorescence was seen most distinctly at the edges of cells but not in the nucleus or cytoplasm. This suggests that the expressed fusion protein is localized to the cell membrane. The results taken together indicate that both the IgK leader sequence and the HA domain have maintained their normal functions in the fusion protein.

Receptor Binding

In order to confirm the proper functioning of the SSTR2 portion of the fusion protein, receptor binding assays were performed using clones and labeled octreotide. Receptor saturation has been reported to occur at $1 \times 10^{-7}$M octreotide (Reisine, et al., Mol. Pharm. 44:1008-1015 (1993); Raynor, et al., Mol. Pharm. 43:838-844 (1993)). Binding of the different clones to $10^{-7}$M $^{111}$In-octreotide was compared in the presence and absence of $10^{-6}$M somastostin-28. Because saturating levels of ligand were used, differences in receptor binding should be due to protein expression. It was found that clones containing the full length SSTR2A chimeric gene (clones 21, 11 and 3) and those with C-terminus intracellular domain deletions (clone tail-1 and tail-4) exhibited more counts per minute without the addition of cold somastotin-28 then with its addition. Specific binding to $^{111}$In-octreotide was greater for clone 21 than 3 than 11 and is similar between clones tail-1 and 11 and between clones tail-4 and 21. Similarly low counts were seen for all clones in the presence of somatostatin-28. As expected, these same low counts were found in cells transfected with vector or untransfected cells with or without addition of somatostatin-28. The findings demonstrate that the SSTR2A domain of the fusion protein is functional and that the intracellular tail of the receptor is not necessary for the binding of octreotide or somastotin-28. In addition, the receptor binding data correlates with the data obtained using Western blots. Thus, the results obtained using the HA tag corroborate the receptor-ligand binding data based on SSTR2A.

Imaging and Biodistribution

Nude mice injected with clones 21, 3, 11 or vector-transfected cells were imaged 4 and 24 hours after the administration of $^{111}$In-octreotide via the tail vein. Only background activity, no tumors, was apparent 4 hours after injection. After 24 hours, tumors derived from vector-transfected cells were not visible and those from clone 11 were difficult to see. In contrast, tumors derived from clone 21 were clearly visible and, to a lesser extent, those from clone 3 were also apparent.

The mice were sacrificed to evaluate biodistribution. This revealed that the greatest radioactivity/gram was in tumors derived from clone 21, followed by clone 3, clone 11 and, finally, by cells transfected with vector alone. This data correlates well with that obtained by ELISA, dot blots, Western blots, receptor binding assays and imaging.

A second group of mice were injected with cells transfected with vector alone, or with the clones tail-4, tail-1, or 11. These mice were imaged in the same manner as described above. After 4 hours, only background radioactivity was apparent. After 24 hours, tumors derived from vector-transfected cells were still not visible and those from clone 11 were difficult to see. In comparison, tumors derived from clone tail-4 and tail-1 were clearly visible, with those derived from tail-1 more apparent than those derived from tail-1. Thus, in vivo, it is possible to non-invasively image cells expressing a fusion protein containing a portion of SSTR2A.

These mice were also sacrificed to evaluate biodistribution, which confirmed the imaging findings. In comparing uptake between the mice in group one (full length SSTR2A fusion protein) and two (full length SSTR2A fusion protein and C-terminus cytoplasmic domain deleted), greater radiotracer uptake was seen in tumors derived from clone tail-1 than clone 11; although, they exhibit similar levels of receptor expression and ligand binding. Indeed tumors derived from tail-1 biodistribution were similar to tumors derived from clone 21, which has greater expression. In addition, greater biodistribution is seen in tumors derived from tail-4 than clone 21, although they exhibit similar expression levels and receptor binding. Uptake in the organs is similar in the two experiments. Thus, the intracellular C-terminus deletion appears to increase specific $^{111}$In-octreotide localization. This is likely secondary to increased ligand internalization and/or retention. Thus, the method allows comparison of mutants while normalizing for gene expression. Further, the data demonstrates that the entire SSTR2 is not needed for visualization in vivo. Smaller SSTR mutants are desirable because of limited space for insertion of genes of interest in many gene transfer vectors.

Biodistribution experiments were also performed using doses of radiotracer similar to those used in humans. To further test the robustness of the method, cells with the least fusion protein expression were employed. As with larger doses of radiotracer, organ radiotracer uptake in the mice mimics clinical findings in humans. Radioactivity per gram is greatest in the kidneys, followed by the liver, gastrointestinal tract, lungs and spleen. In comparison, blood and muscle uptake per gram was quite low. Tumors derived from clone 11 had more uptake of radiotracer/gram than tumors derived from cells transfected with vector only. The data imply that gene transfer using the fusion proteins can be followed with doses of $^{111}$In-octreotide presently used in humans.

Discussion

The data obtained demonstrate that the transfer of SSTR2 gene chimera can be detected in vivo and in vitro. In addition, it was found that the different domains of the expressed fusion protein retain their function. At its amino terminus, the expressed protein contains a 5' IgK leader sequence for membrane localization and a hemagglutinin A tag for detection by anti-HA antibody. It was found that the SSTR2A portion of the fusion protein continues to bind octreotide.

Somatostatin receptor C-terminal fusion proteins have been studied in vitro (Roth, et al., *DNA and Cell Biol.* 16:111-119 (1997)). However, amino terminal fusion was chosen for the present invention because the binding domain for octreotide is distal, predicted to primarily involve SSTR2 amino acids between transmembrane domains three to seven (Liapakis, et al., *J. Biol. Chem.* 271:20331-20339 (1996); Fitzpatrick, et al., *J. Biol. Chem.* 269:24621-24626 (1994); Kaupmann, et al., *EMBO* 14:727-735 (1995)). Although the membrane localization signal at the SSTR2A amino terminus is disrupted by the fusion, a new membrane localization signal is created by the IgK leader sequence. In addition, amino terminal fusion is less likely to interfere with receptor internalization, which involves the carboxy terminal intracellular domain (Koenig, et al., *Biochem. J* 336:291-298). In order to prevent the expression of vector sequences fused to the carboxy terminus, a stop codon was introduced into the PCR reverse primer after the last codon for SSTR2A.

The second portion of the heterologous protein, the HA domain, was exploited for the purpose of confirming expression. In this regard, an ELISA assay allowed for the quick screening of small numbers of cells, thereby saving time usually needed to expand large numbers of resistant colonies. Moreover, the initial screen was performed without utilizing radioactivity. Again capitalizing on the HA domain, immunofluorescence localized the fusion protein to the cell membrane, verifying the presence of a functional leader sequence. Proteins and protein segments may be used as tags. Tags, such as HA, myc, $(His)_6$ and others known in the art, may be used to enhance the assay of a SSTR receptor fusion protein. The tags may be used to nonnalize for protein expression and allow the characterization of various SSTR fusion variants, individually or en masse.

Protein expression was also detected by Western blots. The expressed protein has an apparent molecular weight of 72,000 Da for the full length SSTR2A insert and 70,000 Da for the intracellular tail minus insert. These values are less than those previously reported for SSTR2A and greater than predicted for the protein components alone. Previous studies have shown that wild type SSTR2 s glycosylated. Thus, discrepancies in molecular weights may be due to the Igk leader sequence and HA domain altering the normal glycosylation of the receptor. Because somatostatin-28 inhibits binding of $^{111}$In-octreotide to cells expressing the fusion protein, the data imply that the presumed modifications in glycosylation do not interfere with ligand binding.

The examples discussed herein demonstrate that the three portions of the expressed fusion protein are functional and that in vitro expression data correlate with in vivo imaging and biodistribution data. The intracellular carboxy terminus is not necessary for imaging SSTR2A or detecting the fusion protein in vitro or in vivo. Indeed, in vivo, deletion of the carboxy terminus intracellular domain appears to increase radiotracer localization. Thus, data suggest that it is possible to create receptor mutants or chimeric receptor mutants for increased specific radiopharmaceutical localization. The method allows comparison of mutants while normalizing for gene expression. Visualization of the carboxy terminus deleted receptors in vivo demonstrates that the method enables creation of mutants with desirable properties such as a decreased size of insert. In addition, it was found that imaging in animals can be effectively accomplished at doses of $^{111}$In-octreotide that are similar on a per gram basis to those used in humans. Thus, non-invasive detection of gene transfer, including chimeric gene transfer, may be feasible clinically.

All references cited herein are fully incorporated by reference. Having now fully described the invention, it will be understood by one of skill in the art that the invention may be performed within a wide and equivalent range of conditions, parameters and the like, without affecting the spirit or scope of the invention or any embodiment thereof.

Accession numbers for human and rat mRNA for Somatostatin Receptors are as follows: Human: SSTR1=NM_001049; SSTR2=NM_001050; SSTR3=NM_001051; SSTR4=NM_001052; SSTR5=NM_001053. Rat: SSTR1=NM_012719; SSTR2=NM_019348; SSTR4=NM_013036; SSTR5=NM_012882.

What is claimed is:

1. A fusion protein comprising:
   a) a somatostatin receptor polypeptide, the somatostatin receptor polypeptide being truncated at its C-terminus relative to wild-type somatostatin receptor; and
   b) a heterologous polypeptide fused to the N-terminus, if not truncated, or the trucated N-terminus, if truncated, or truncated C-terminus of said somatostatin receptor polypeptide:
   wherein:
   i) the C-terminus of said somatostatin receptor polypeptide is truncated at amino acid 314;
   ii) the somatostatin receptor polypeptide is also truncated at its N-terminus;
   iii) the fusion protein comprises a leader sequence fused to the truncated C-terminus of said somatostatin receptor polypeptide;
   iv) the heterologous polypeptide is a protein fusion tag that is hemagglutinin A or has enzymatic activity; or
   v) the fusion protein comprises a leader sequence that is an IgK leader sequence.

2. The fusion protein of claim 1, wherein the C-terminus of said somatostatin receptor polypeptide is truncated at amino acid 314.

3. The fusion protein of claim 1, wherein the somatostatin receptor polypeptide is also truncated at its N-terminus.

4. The fusion protein of claim 1, wherein said heterologous polypeptide is fused to the truncated C-terminus of the somatostatin receptor polypeptide.

5. The fusion protein of claim 1, wherein said heterologous polypeptide is fused to the N-terminus of the somatostatin receptor polypeptide.

6. The fusion protein of claim 1, wherein said somatostatin receptor polypeptide is a somatostatin type 2 receptor polypeptide.

7. The fusion protein of claim 1, further comprising a leader sequence fused to said somatostatin receptor polypeptide.

8. The fusion protein of claim 7, wherein the leader sequence is fused to the N-terminus of said somatostatin receptor polypeptide or the heterologous polypeptide.

9. The fusion protein of claim 7, wherein the leader sequence is fused to the truncated C-terminus of said somatostatin receptor polypeptide.

10. The fusion protein of claim 1, wherein said heterologous polypeptide is a protein fusion tag.

11. The fusion protein of claim 10, wherein said heterologous polypeptide is hemagglutinin A.

12. The polypeptide of claim 7, wherein said leader sequence is the Igk leader sequence.

13. The fusion protein of claim 1, wherein said somatostatin receptor polypeptide is a somatostatin type 2 receptor polypeptide comprising a carboxy terminal truncation.

14. The fusion protein of claim 13, wherein said carboxy terminal truncation alters internalization or signaling of said somatostatin type 2 receptor polypeptide into a cell.

15. The fusion protein of claim 10, wherein said fusion protein tag has enzymatic activity.

16. The fusion protein of claim 15, wherein said fusion protein tag is selected from the group consisting of hemagglutinin A, beta-galactosidase, thymidine kinase, transferrin, myc-tag, VP16, $(His)_6$-tag, and chloramphenicol acetyl transferase.

17. The fusion protein of claim 1, wherein the fusion protein is encoded by a nucleic acid.

* * * * *

SEQUENCE LISTING

```
<160> NUMBER OF SEQ ID NOS: 2

<210> SEQ ID NO 1
<211> LENGTH: 27
<212> TYPE: DNA
<213> ORGANISM: Homo sapiens

<400> SEQUENCE: 1
tccccgcggc atggacatgg cggatga                                    27

<210> SEQ ID NO 2
<211> LENGTH: 30
<212> TYPE: DNA
<213> ORGANISM: Homo sapiens

<400> SEQUENCE: 2
aatctgcagc tgtcagatac tggtttggag                                 30
```